US010729388B2

(12) United States Patent
Reihman et al.

(10) Patent No.: US 10,729,388 B2
(45) Date of Patent: Aug. 4, 2020

(54) DEVICES USED IN CONNECTION WITH CONTINUOUS ANALYTE MONITORING THAT PROVIDE THE USER WITH ONE OR MORE NOTIFICATIONS, AND RELATED METHODS

(71) Applicant: DexCom, Inc., San Diego, CA (US)

(72) Inventors: Eli Reihman, San Diego, CA (US); Jennifer Blackwell, San Diego, CA (US); Leif N. Bowman, San Diego, CA (US); Thomas Hall, San Diego, CA (US); Katherine Yerre Grubstein, San Diego, CA (US); Zebediah L. McDaniel, San Diego, CA (US); Matthew D. Wightlin, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 1169 days.

(21) Appl. No.: 14/524,919

(22) Filed: Oct. 27, 2014

(65) Prior Publication Data

US 2015/0119667 A1    Apr. 30, 2015

Related U.S. Application Data

(60) Provisional application No. 61/896,597, filed on Oct. 28, 2013.

(51) Int. Cl.
*A61B 5/00* (2006.01)
*A61B 5/145* (2006.01)
(Continued)

(52) U.S. Cl.
CPC ............ *A61B 5/746* (2013.01); *A61B 5/0002* (2013.01); *A61B 5/0004* (2013.01);
(Continued)

(58) Field of Classification Search
CPC ......... A61B 5/00; A61B 5/145; A61B 5/6802; A61B 5/746; A61B 5/14532; A61B 5/6824; A61B 5/6831; A61B 5/7445; A61B 5/7282; A61B 5/0004; A61B 5/7257; A61B 5/0002; A61B 5/743; G06F 19/3418; G06F 19/3437; G06F 19/3468; G06F 19/3406
See application file for complete search history.

(56) References Cited

U.S. PATENT DOCUMENTS 6,393,318 B1    5/2002   Conn et al.
7,261,691 B1    8/2007   Asomani
(Continued)

FOREIGN PATENT DOCUMENTS

WO    WO 2003-077361   9/2003
WO    WO 2009/105709   8/2009
WO    WO 2010-111660   9/2010

*Primary Examiner* — Eric J Messersmith
(74) *Attorney, Agent, or Firm* — Knobbe, Martens, Olson & Bear, LLP

(57) ABSTRACT

Devices and methods for providing a user with alerts are provided. The alerts may take different forms, such as an output to a display, a speaker, a vibration module, a shock module, etc. The alerts provide the user with sufficient information to take appropriate action, but the devices may be of limited functionality to enhance their compactness, discreetness, wearability, etc., while also lowering their cost to manufacture.

17 Claims, 5 Drawing Sheets

(51) Int. Cl.
   *G06F 19/00*     (2018.01)
   *G16H 40/63*     (2018.01)
   *G16H 50/50*     (2018.01)

(52) U.S. Cl.
   CPC ........ *A61B 5/14532* (2013.01); *A61B 5/6802* (2013.01); *A61B 5/6824* (2013.01); *A61B 5/6831* (2013.01); *A61B 5/7282* (2013.01); *A61B 5/7445* (2013.01); *G06F 19/3468* (2013.01); *G16H 40/63* (2018.01); *A61B 5/7257* (2013.01); *A61B 5/743* (2013.01); *G06F 19/3418* (2013.01); *G16H 50/50* (2018.01); *Y02A 90/26* (2018.01)

(56) References Cited

U.S. PATENT DOCUMENTS

| | | | |
|---|---|---|---|
| 7,689,437 | B1 | 3/2010 | Teller et al. |
| 2003/0208113 | A1 | 11/2003 | Mault et al. |
| 2006/0001538 | A1* | 1/2006 | Kraft .................. A61B 5/14532 340/539.12 |
| 2008/0015422 | A1 | 1/2008 | Wessel |
| 2008/0092638 | A1* | 4/2008 | Brenneman ......... G06F 19/3418 73/61.41 |
| 2009/0221890 | A1 | 9/2009 | Saffer et al. |
| 2011/0193704 | A1 | 8/2011 | Harper et al. |
| 2012/0306643 | A1 | 12/2012 | Dugan |
| 2013/0078912 | A1 | 3/2013 | San Vicente et al. |
| 2014/0375428 | A1* | 12/2014 | Park ................... G06K 7/10237 340/10.1 |
| 2015/0052943 | A1* | 2/2015 | Inglis .................. A44C 5/0069 63/5.1 |

* cited by examiner

DEVICES USED IN CONNECTION WITH CONTINUOUS ANALYTE MONITORING THAT PROVIDE THE USER WITH ONE OR MORE NOTIFICATIONS, AND RELATED METHODS

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 61/896,597, filed Oct. 28, 2013. The aforementioned application is incorporated by reference herein in its entirety, and is hereby expressly made a part of this specification.

TECHNICAL FIELD

The present embodiments relate to continuous analyte monitoring, and more particularly to systems and methods for providing a user with an alert in response to a detected analyte condition.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood glucose, which can cause an array of physiological derangements associated with the deterioration of small blood vessels, for example, kidney failure, skin ulcers, or bleeding into the vitreous of the eye. A hypoglycemic reaction (low blood glucose) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter that transmits measurement data to a receiver that processes and displays information based on the measurements. Such sensor systems are sometimes referred to as continuous glucose monitors (CGMs).

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

The present embodiments have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

In a first aspect, which is generally applicable (i.e. independently combinable with any of the aspects or embodiments identified herein), particularly with any other embodiment of the first aspect, certain of the present embodiments comprise a wearable device for providing an alert to a user regarding the user's blood glucose value. The device comprises a communication module for receiving a signal from a transmitter of a continuous glucose monitoring (CGM) device. The device further comprises an alert interface configured to provide a first alert when the wearer's blood glucose value is within a predetermined range, and a second alert that the wearer's blood glucose value is outside the predetermined range.

In an embodiment of the first aspect, the alert interface comprises at least one of a display, a vibration module, and a shock module.

In an embodiment of the first aspect, the device further comprises a band configured to be worn about a wrist of a wearer, wherein the communication module and the alert interface are incorporated into the band.

In an embodiment of the first aspect, the band comprises a closed loop having no endpoints.

In an embodiment of the first aspect, the band is constructed of a resilient material.

In an embodiment of the first aspect, the alert interface comprises a display including at least one of a liquid crystal display (LCD), one or more light-emitting diodes (LEDs), one or more organic light-emitting diodes (OLEDs), an electronic paper display, a color- or pattern-changing material, or a text display.

In an embodiment of the first aspect, wherein the communication module is configured to relay the signal received from the transmitter to another electronic device.

In an embodiment of the first aspect, the communication module is configured to store data received from the transmitter and relay the data to the other electronic device at regular intervals.

In an embodiment of the first aspect, the device is configured to process or partially process the data prior to relaying it to the other electronic device.

In an embodiment of the first aspect, the communication module is configured to store data received from the transmitter and relay the data to the other electronic device when the user requests.

In an embodiment of the first aspect, a user request to relay the data may be initiated using the device.

In an embodiment of the first aspect, the communication module is configured to relay the signal received from the transmitter to the another electronic device at regular intervals.

In an embodiment of the first aspect, the regular intervals comprise every 30 seconds, every 60 seconds, every 90 seconds, every 2 minutes, every 3 minutes, every 5 minutes, every 10 minutes, every 15 minutes, every 20 minutes, or every 30 minutes.

In an embodiment of the first aspect, the communication module is configured to relay the signal received from the transmitter to the another electronic device in response to a trigger.

In an embodiment of the first aspect, the trigger comprises a user request, a glucose concentration, a change in state or zone or range of a glucose concentration, or glucose information meeting one or more predetermined criteria.

In an embodiment of the first aspect, the criteria are user-defined.

In an embodiment of the first aspect, the device further comprises a controller configured to control operation of the communication module and/or the alert interface.

In an embodiment of the first aspect, the controller comprises at least one of a processor, a microprocessor, a programmable logic controller, or an application specific integrated circuit (ASIC).

In an embodiment of the first aspect, the device further comprises a power source configured to power the communication module and/or the alert interface.

In an embodiment of the first aspect, the power source comprises a rechargeable and/or replaceable battery.

In an embodiment of the first aspect, a functionality of the alert interface is limited to changing color in response to the signal received from the transmitter.

In an embodiment of the first aspect, the alert interface is configured to display a first color when the signal indicates that the user's blood glucose is within an acceptable range, and display a second color when the signal indicates that the user's blood glucose is outside the acceptable range.

In an embodiment of the first aspect, the alert interface is configured to display a first color and/or a first blink pattern when the signal indicates that the user's blood glucose is within a first narrower range, display a second color and/or a second blink pattern when the signal indicates that the user's blood glucose is outside the first narrower range, but still within a second wider range, and display a third color and/or a third blink pattern when the signal indicates that the user's blood glucose is outside the second wider range.

In an embodiment of the first aspect, a functionality of the alert interface is limited to displaying a trend arrow indicating whether the user's current blood glucose value is rising or falling, wherein the trend arrow points upward to indicate a rising value and downward to indicate a falling value In an embodiment of the first aspect, a functionality of the alert interface is limited to displaying nothing more than text that provides an indication of the user's current blood glucose value.

In an embodiment of the first aspect, the text consists of "high," "normal," and "low."

In an embodiment of the first aspect, the text consists of a number corresponding to the user's current blood glucose value.

In an embodiment of the first aspect, the number is color coded.

In an embodiment of the first aspect, the number is a first color when the user's blood glucose is within an acceptable range, and a second color when the user's blood glucose is outside the acceptable range.

In an embodiment of the first aspect, a functionality of the alert interface is limited to displaying one or more lights that remain solid or blink in response to the signal received from the transmitter.

In an embodiment of the first aspect, the alert interface comprises three lights, and a single blinking light indicates a hypoglycemic condition, a single solid light indicates a low glucose condition, two solid lights indicate that glucose is in a target range, three solid lights indicate a high glucose condition, and three blinking lights indicate a hyperglycemic condition.

In an embodiment of the first aspect, the lights comprise light-emitting diodes (LEDs).

In an embodiment of the first aspect, a functionality of the alert interface is limited to displaying a progression of lights illuminating and darkening to indicate a rate of change of the user's blood glucose value.

In an embodiment of the first aspect, the lights flash from left to right or bottom to top to indicate rising glucose, and flash from right to left or top to bottom to indicate falling glucose.

In an embodiment of the first aspect, a functionality of the alert interface is limited to providing positive feedback when the user's blood glucose remains within a desired glucose range for a set period of time, and providing negative feedback when the user's blood glucose is outside the desired glucose range.

In an embodiment of the first aspect, the alert interface is configured to display how many days have passed without a high glucose event or a low glucose event.

In an embodiment of the first aspect, the alert interface is configured to provide a numerical indication of how many high glucose events and/or low glucose events have occurred within a given interval.

In an embodiment of the first aspect, the alert interface is configured to provide a numerical indication of an amount of time the user has spent within a desired glucose range.

In an embodiment of the first aspect, the device is configured to emit one or more audible tones.

In an embodiment of the first aspect, a volume of the tones increases over time until the user takes action.

In an embodiment of the first aspect, the alert interface comprises one or more light pipes including a tubular portion defining a lumen.

In an embodiment of the first aspect, a first end of the tubular portion receives light from a light source within the device.

In an embodiment of the first aspect, the light travels through the lumen and is visible at a second end of the tubular portion that is exposed to the exterior of the device.

In an embodiment of the first aspect, the alert is configurable by the user.

In an embodiment of the first aspect, an intensity of the alert is programmable so that it can vary according to time of day.

In an embodiment of the first aspect, the device is configured to communicate with a network of other devices associated with other users.

In an embodiment of the first aspect, the device is configured to provide the user with location information, such as locations of the other users in the network.

In an embodiment of the first aspect, the alert interface comprises a vibration module configured to increase an intensity of vibration over time until the user takes action.

In an embodiment of the first aspect, the alert interface comprises a vibration module configured to pulse vibrations in different patterns to indicate different alarms.

In an embodiment of the first aspect, the communication module receives the signal from the CGM device and forwards data from the signal to another device.

In an embodiment of the first aspect, the communication module receives the signal from the CGM device using a first wireless communication protocol and forwards the data from the signal to the another device using a second, different, wireless communication protocol.

In an embodiment of the first aspect, the first wireless protocol is a proprietary wireless protocol, and the second wireless protocol is a standardized wireless protocol.

In an embodiment of the first aspect, the first wireless protocol is a first standardized wireless protocol, and the second wireless protocol is a second, different, standardized wireless protocol.

In an embodiment of the first aspect, the device is configured to be in physical contact with skin of a wearer at all times when worn by the wearer.

In an embodiment of the first aspect, the communication module receives the signal from the CGM device at regular intervals.

In an embodiment of the first aspect, the regular intervals comprise every 30 seconds, every 60 seconds, every 90 seconds, every 2 minutes, every 3 minutes, every 5 minutes, every 10 minutes, every 15 minutes, every 20 minutes, or every 30 minutes.

In an embodiment of the first aspect, the communication module receives the signal from the CGM device in response to a trigger.

In an embodiment of the first aspect, the trigger comprises a user request, a glucose concentration, a change in state or zone or range of a glucose concentration, or glucose information meeting one or more predetermined criteria.

In an embodiment of the first aspect, the criteria are user-defined.

In an embodiment of the first aspect, the communication module is configured to request transmission the signal from the CGM device responsive to an amount of time since a last transmission was received.

In an embodiment of the first aspect, the communication module is configured to request transmission the signal from the CGM device responsive to a user request.

In a second aspect, which is generally applicable (i.e. independently combinable with any of the aspects or embodiments identified herein), particularly with any other embodiment of the first aspect, certain of the present embodiments comprise a method of providing an alert to a user regarding the user's blood glucose value. The method comprises receiving a signal providing information about the user's current blood glucose value. The method further comprises providing a first alert when the user's current glucose concentration is within a predetermined range, and a second alert when the user's current glucose concentration is outside the predetermined range.

In an embodiment of the second aspect, an alert interface comprising at least one of a display, a vibration module, and a shock module provides the first alert and the second alert.

In an embodiment of the second aspect, the method further comprises relaying the signal to an electronic device.

In an embodiment of the second aspect, the method further comprises storing data received from the signal and relaying the data to the electronic device at regular intervals.

In an embodiment of the second aspect, the method further comprises processing or partially processing the data prior to relaying it to the electronic device.

In an embodiment of the second aspect, the method further comprises storing data received from the signal and relaying the data to the electronic device when the user requests.

In an embodiment of the second aspect, the signal is received using a first wireless communication protocol and relayed using a second, different, wireless communication protocol.

In an embodiment of the second aspect, the first wireless protocol is a proprietary wireless protocol, and the second wireless protocol is a standardized wireless protocol.

In an embodiment of the second aspect, the first wireless protocol is a first standardized wireless protocol, and the second wireless protocol is a second, different, standardized wireless protocol.

In an embodiment of the second aspect, the method further comprises the user configuring the alert.

In an embodiment of the second aspect, the method further comprises the user programming an intensity of the alert so that it varies according to time of day.

In an embodiment of the second aspect, the method further comprises communicating with a network of other devices associated with other users.

In an embodiment of the second aspect, the method further comprises providing the user with location information, such as locations of the other users in the network.

Any of the features of embodiments of the various aspects disclosed is applicable to all aspects and embodiments identified. Moreover, any of the features of an embodiment is independently combinable, partly or wholly with other embodiments described herein, in any way, e.g., one, two, or three or more embodiments may be combinable in whole or in part. Further, any of the features of an embodiment of the various aspects may be made optional to other aspects or embodiments. Any aspect or embodiment of a method can be performed by a system or apparatus of another aspect or embodiment, and any aspect or embodiment of the system can be configured to perform a method of another aspect or embodiment.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

The present embodiments now will be discussed in detail with an emphasis on highlighting the advantageous features. These embodiments depict the novel and non-obvious devices and methods shown in the accompanying drawings, which are for illustrative purposes only. These drawings include the following figures, in which like numerals indicate like parts.

DETAILED DESCRIPTION

Figure 1:
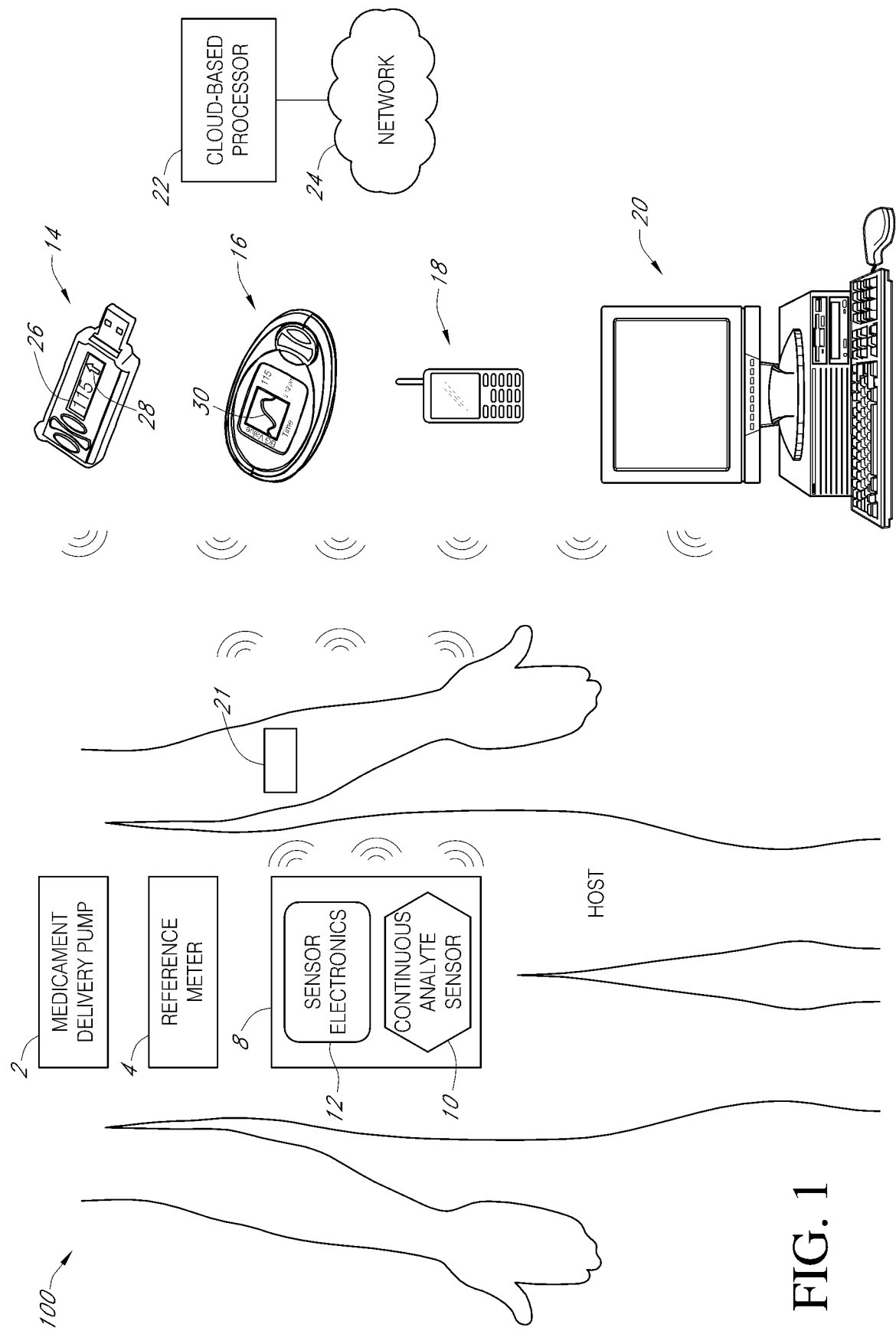
FIG. 1 is a schematic view of a continuous analyte sensor system attached to a host and communicating with other devices.

The following detailed description describes the present embodiments with reference to the drawings. In the drawings, reference numbers label elements of the present embodiments. These reference numbers are reproduced below in connection with the discussion of the corresponding drawing features.

The drawings and their descriptions may indicate sizes, shapes and configurations of the various components. Such depictions and descriptions should not be interpreted as limiting. Alternative sizes, shapes and configurations are also contemplated as within the scope of the present embodiments. Also, the drawings, and their written descriptions, indicate that certain components of the apparatus are formed integrally, and certain other components are formed as separate pieces. Components shown and described herein as being formed integrally may in alternative embodiments be formed as separate pieces. Further, components shown and described herein as being formed as separate pieces may in alternative embodiments be formed integrally. As used herein the term integral describes a single unitary piece.

The preferred embodiments relate to the use of an analyte sensor that measures a concentration of glucose or a substance indicative of the concentration or presence of the analyte. In some embodiments, the analyte sensor is a continuous device, for example a subcutaneous, transdermal, transcutaneous, and/or intravascular (e.g., intravenous) device. In some embodiments, the device can analyze a plurality of intermittent blood samples. The analyte sensor can use any method of glucose-measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The analyte sensor can use any known method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor, the systems and methods of the preferred embodiments can be applied to any measurable analyte. In some preferred embodiments, the analyte sensor is a glucose sensor capable of measuring the concentration of glucose in a host. One example embodiment is described below, which utilizes an implantable glucose sensor. However, it should be understood that the devices and methods described herein can be applied to any device capable of detecting a concentration of analyte and providing an output signal that represents the concentration of the analyte.

In one preferred embodiment, the analyte sensor is an implantable glucose sensor, such as described with reference to U.S. Pat. No. 6,001,067 and U.S. Patent Publication No. US-2011-0027127-A1. In another preferred embodiment, the analyte sensor is a transcutaneous glucose sensor, such as described with reference to U.S. Patent Publication No. US-2006-0020187-A1. In yet another preferred embodiment, the analyte sensor is a dual electrode analyte sensor, such as described with reference to U.S. Patent Publication No. US-2009-0137887-A1. In still other embodiments, the sensor is configured to be implanted in a host vessel or extracorporeally, such as is described in U.S. Patent Publication No. US-2007-0027385-A1.

The term "analyte" as used herein is a broad term, and is to be given its ordinary and customary meaning to a person of ordinary skill in the art (and it is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to lactate or lactic acid; cardiac markers; ketone bodies; acetone; acetoacetic acid; beta hydroxybutyric acid; glucagon, acetyl Co A; intermediaries in the Citric Acid Cycle; choline, testosterone; creatinine; triglycerides; sodium; potassium; chloride; bicarbonate; total protein; alkaline phosphatase; calcium; phosphorus; $PO_2$; $PCO_2$; bilirubin (direct and total); red blood cell count; white blood cell count; hemoglobin; hemactocrit; lymphocytes; monocytes; eosinophils; basophils; c-reactive protein; cryoglobulins; fibrinogens; ACTH; aldosterone; ammonia; beta-HCG; magnesium; copper; iron; total cholesterol; low density lipoproteins; high density lipoproteins; lipoprotein A; T4 (total and free); TSH; FSH; LH; ACTH; hepatitis BE antigen; hepatitis B surface antigen; hepatitis A antibody; hepatitis C antibody; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies A, S, C, and E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium fal-*

*ciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

For illustrative purposes, reference will now be made to FIG. 1, which is an example environment in which some embodiments described herein may be implemented. Here, an analyte monitoring system 100 includes a continuous analyte sensor system 8. Continuous analyte sensor system 8 includes a sensor electronics module 12 and a continuous analyte sensor 10. The system 100 can also include other devices and/or sensors, such as a medicament delivery pump 2 and a reference analyte meter 4, as illustrated in FIG. 1. The continuous analyte sensor 10 may be physically connected to sensor electronics module 12 and may be integral with (e.g., non-releasably attached to) or releasably attachable to the continuous analyte sensor 10. Alternatively, the continuous analyte sensor 10 may be physically separate to sensor electronics module 12, but electronically coupled via inductive coupling or the like. Further, the sensor electronics module 12, medicament delivery pump 2, and/or analyte reference meter 4 may communicate with one or more additional devices, such as any or all of display devices 14, 16, 18, 20, and/or one or more wearable devices 21.

The system 100 of FIG. 1 also includes a cloud-based processor 22 configured to analyze analyte data, medicament delivery data, and/or other patient related data provided over network 24 directly or indirectly from one or more of sensor system 8, medicament delivery pump 2, reference analyte meter 4, display devices 14, 16, 18, 20, and wearable device 21. Based on the received data, the processor 22 can further process the data, generate reports providing information based on the processed data, trigger notifications to electronic devices associated with the host or caretaker of the host, or provide processed information to any of the other devices of FIG. 1. In some example implementations, the cloud-based processor 22 comprises one or more servers. If the cloud-based processor 22 comprises multiple servers, the servers can be either geographically local or separate from one another. The network 24 can include any wired and wireless communication medium to transmit data, including WiFi networks, cellular networks, the Internet and any combinations thereof.

It should be understood that although the example implementation described with respect to FIG. 1 refers to analyte data being received by processor 22, other types of data processed and raw data may be received as well.

In some example implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor.

The sensor electronics module 12 may, as noted, couple (e.g., wirelessly and the like) with one or more devices, such as any or all of display devices 14, 16, 18, 20, and wearable device 21. The display devices 14, 16, 18, 20 may be configured for processing and presenting information, such as sensor information transmitted by the sensor electronics module 12 for display at the display device. The display devices 14, 16, 18, 20, and/or the wearable device 21 may also trigger alarms based on the analyte sensor data.

The wearable device 21 may also be configured for processing and presenting information, such as sensor information transmitted by the sensor electronics module 12. The wearable device 21 may include an alert interface. The alert interface may comprise, for example, a display, a vibration module, a shock module, a speaker, and/or any other type of device that is capable of providing the user with physiological information.

In FIG. 1, display device 14 is a key fob-like display device, display device 16 is a hand-held application-specific computing device 16 (e.g. the DexCom G4® Platinum receiver commercially available from DexCom, Inc.), display device 18 is a general purpose smart phone or tablet computing device 20 (e.g. an Apple® iPhone®, iPad®, or iPod Touch® commercially available from Apple, Inc.), display device 20 is a computer workstation 20, and wearable device 21 is any device that is worn on, or integrated into, a user's vision, clothes, and/or bodies. In some example implementations, the relatively small, key fob-like display device 14 may be a computing device embodied in a wrist watch, a belt, a necklace, a pendent, a piece of jewelry, an adhesive patch, a pager, a key fob, a plastic card (e.g., credit card), an identification (ID) card, and/or the like. In some example implementations, the wearable device 21 may comprise anklets, glasses, rings, necklaces, arm bands, pendants, belt clips, hair clips/ties, pins, cufflinks, tattoos, stickers, socks, sleeves, gloves, garments (e.g. shirts, pants, underwear, bra, etc.), "clothing jewelry" such as zipper pulls, buttons, watches, shoes, contact lenses, subcutaneous implants, cochlear implants, shoe inserts, braces (mouth), braces (body), medical wrappings, sports bands (wrist band, headband), hats, bandages, hair weaves, nail polish, artificial joints/body parts, orthopedic pins/devices, implantable cardiac or neurological devices, etc. The small display device 14 and/or the wearable device 21 may include a relatively small display (e.g., smaller than the display device 18) and may be configured to display graphical and/or numerical representations of sensor information, such as a numerical value 26 and/or an arrow 28. In contrast, the display devices 16, 18, and 20 can be larger display devices that can be capable of displaying a larger set of displayable information, such as a trend graph 30 depicted on the hand-held receiver 16 in addition to other information such as a numerical value and arrow.

In various embodiments, the wearable device 21 may be attached to the wearer and/or to his or her clothing in any convenient fashion. For example, the wearable device 21 may encompass a body part of the wearer, such as an arm, a leg, the neck, etc. Instead, or in addition, the wearable device 21 may be secured to the wearer's skin with adhesive. In embodiments including a vibration module, a shock module, or any other device that provides the wearer with tactile feedback, these embodiments may be most effective if the wearable device 21 is directly or indirectly touching the wearer's skin in such a way that vibrations, shocks, etc. can be felt by the wearer. For example, directly securing the wearable device 21 to the wearer's skin with adhesive may be advantageous.

It is understood that any other user equipment (e.g. computing devices) configured to at least present information (e.g., a medicament delivery information, discrete self-monitoring analyte readings, heart rate monitor, caloric intake monitor, and the like) can be used in addition or instead of those discussed with reference to FIG. 1.

In some example implementations of FIG. 1, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations of FIG. 1, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

In some implementations of FIG. 1, the continuous analyte sensor system 8 includes a DexCom G4® Platinum glucose sensor and transmitter commercially available from DexCom, Inc., for continuously monitoring a host's glucose levels.

Under certain circumstances, a user may not need detailed information about his or her current blood glucose. For example, those who suffer from type 2 diabetes generally only need to know if their current blood glucose is high, low, or within an acceptable range, but don't necessarily need to know the precise value of their blood glucose at any given moment, or how it has fluctuated over time. For such people, a typical CGM receiver provides more information than needed, and therefore can be cumbersome to carry around, may limit the user's activities, and/or may cause embarrassment for the user in social situations. Also, even for people who routinely rely on a typical CGM receiver, that receiver may not always be available. Thus, it would be advantageous to provide users with a low level or intermediate level of information when detailed information is not needed or the user's receiver is not available. The information can then be transmitted to a receiver or elsewhere at a later time. Certain of the present embodiments address this issue by providing a device having limited functionality that can be worn discreetly, but that still provides the user with a minimum quantum of information regarding his or her blood glucose. For example, the information provided may relate to blood glucose thresholds and/or rates of change.

Figure 2:
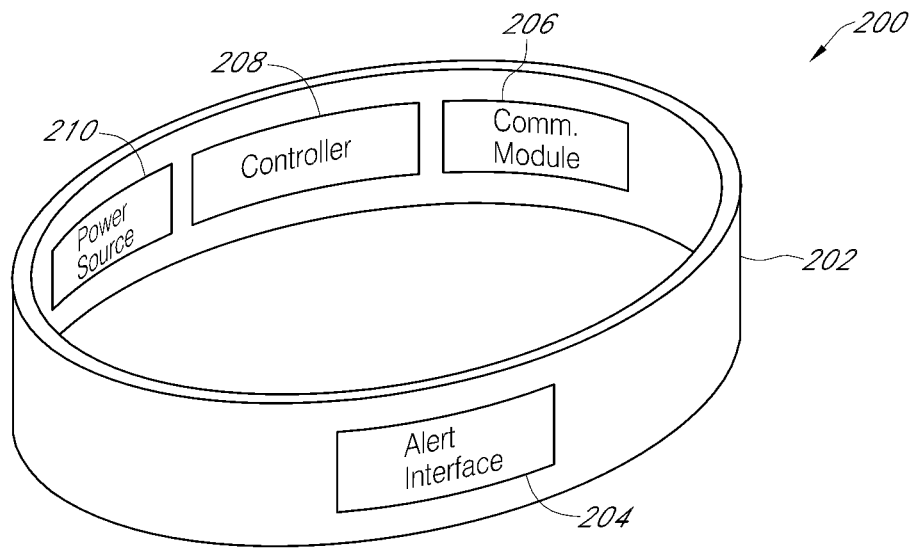
FIG. 2 is a front perspective view of one embodiment of a wearable device for providing a user with an alert.

With reference to FIG. 2, one of the present embodiments comprises a wearable device 200. The wearable device 200 may comprise any of the wearable devices described herein, such as anklets, glasses, rings, necklaces, arm bands, pendants, belt clips, hair clips/ties, pins, cufflinks, tattoos, stickers, socks, sleeves, gloves, garments (e.g. shirts, pants, underwear, bra, etc.), "clothing jewelry" such as zipper pulls, buttons, watches, shoes, contact lenses, subcutaneous implants, cochlear implants, shoe inserts, braces (mouth), braces (body), medical wrappings, sports bands (wrist band, headband), hats, bandages, hair weaves, nail polish, artificial joints/body parts, orthopedic pins/devices, implantable cardiac or neurological devices, etc. In the illustrated embodiment, the wearable device 200 comprises a closed loop band 202 having no endpoints and sized to be comfortably worn about the wrist, ankle, etc. The band 202 may be constructed of flexible and resilient material such that it can stretch to be slipped over the hand or foot. Example materials include rubbers of various types (e.g. vulcanized, butadiene, etc.), silicone, latex, nylon, polyester, leather, steel, string/cord, other plastics (acrylic, polycarbonate, polyesters, polyethylene, polypropylene, ABS, etc.), ceramic, etc. In alternative embodiments, the band 202 may not be a closed loop. Instead, the band 202, made from any material, may comprise first and second ends that are releasably securable to one another with a buckle, clasp, etc.

The wearable device 200 comprises an alert interface 204 that is configured to provide the user with an alert and/or other information about one or more of his or her physiologic conditions. For example, glucose and activity levels could be combined in a simple display to aid diabetics and/or athletes in managing glucose levels. The examples described herein relate to the user's blood glucose, but the present embodiments are not limited to these examples, and could include any physiologic conditions or combination of conditions.

The alert interface 204 may comprise, for example, a display, a vibration module, a shock module, a speaker, and/or any other type of device that is capable of providing the user with physiological information. In embodiments in which the alert interface 204 includes a display, the display may comprise any of a plurality of different types of displays, including but not limited to a liquid crystal display (LCD), one or more light-emitting diodes (LEDs), one or more organic light-emitting diodes (OLEDs), an electronic paper display, e-ink, a color- or pattern-changing material, magnetic materials, piezo-electric materials, vibration patterns, heat/cold patterns, one or more light pipes with single-color or multicolor LED(s) or OLED(s), transparent and flexible multi-touch surfaces, such as those available from 3M, interactive glass surfaces, such as those available from Corning, etc. In further embodiments, the wearable device may not include a discrete display. Rather, the wearable device itself may be a display that presents information by, for example, changing the color of the entire wearable device.

The wearable device 200 may further include a button (not shown) to activate and/or deactivate the alert interface 204. A button could also be provided to power down the wearable device. Powering down may be useful during activities where the user knows his or her blood glucose is unlikely to rise or fall significantly. For example, before and/or during exercise a user may preemptively take insulin or eat food to correct for an expected change in blood glucose, and the user may therefore want to clear any alarms or turn the wearable device 200 off altogether. The button may also be useful to initiate data communication between the wearable device and the sensor system 8, for example, to provide data transfer on-demand.

Figure 5:
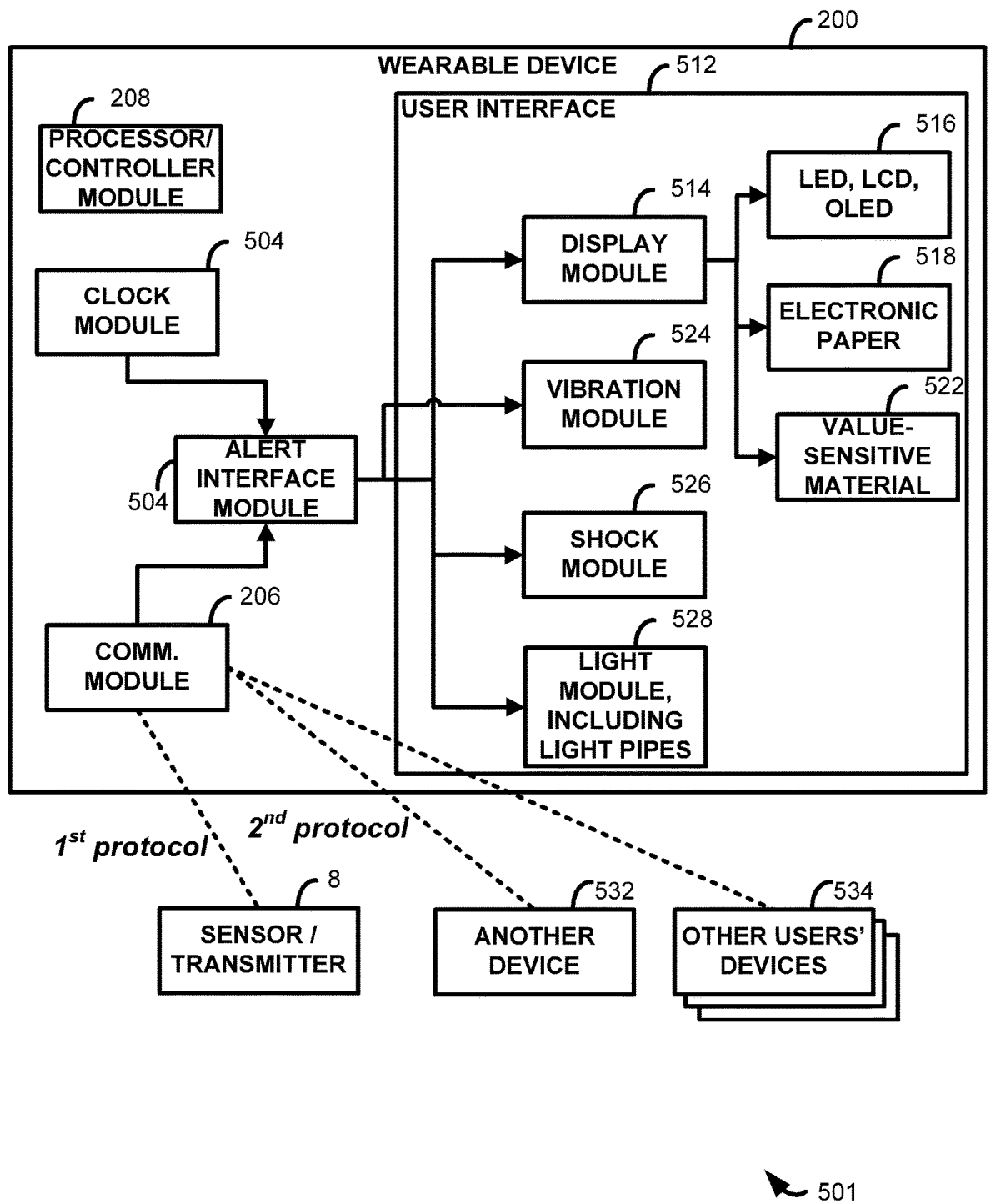
FIG. 5 is a system diagram illustrating various components within an embodiment of a wearable device for providing a user with an alert.

Referring to FIG. 1 as well as to the expanded system diagram 501 of FIG. 5, the wearable device 200 further comprises a communication module 206, which enables the wearable device 200 to receive information about the user's blood glucose from the sensor electronics unit 12 of the on-skin sensor assembly 8 (FIG. 1). The communication module 206 may include an antenna (not shown) and any other hardware and circuitry necessary for receiving and processing a signal output by the sensor electronics unit 12. The wearable device 200 further comprises a controller 208 for controlling operation of the alert interface 204 (implemented in FIG. 5 as an alert interface module 504) and the communication module 206. The controller 208 may include one or more of a processor, a microprocessor, a programmable logic controller, an application specific integrated circuit (ASIC), a system on a chip (SoC), a programmable system-on-chip (PSoC), etc. The wearable device 200 further comprises a power source 210, such as a battery, for powering the alert interface 204, the communication module 206, and/or the controller 208. In some embodiments, the power source 210 may be a rechargeable and/or replaceable battery. In one particular embodiment, the battery may be recharged via a universal serial bus (USB) connection (not shown) that allows information to be transferred from the wearable device 200 to another device, such as a computer (not shown).

In some embodiments, analyte information may be transmitted from the sensor electronics unit 12 and/or received by the wearable device 200 at regular intervals, such as every 30 seconds, every 60 seconds, every 90 seconds, every 2 minutes, every 3 minutes, every 5 minutes, every 10 minutes, every 15 minutes, every 20 minutes, every 30 minutes, or at any other regular interval. Also in some embodiments, analyte information may be transmitted from the sensor electronics unit 12 and/or received by the wearable device 200 in response to a trigger. A variety of triggers are contemplated. For example, analyte information may be transmitted and/or received whenever the user requests. In other examples, a transmission from the sensor electronics unit 12 may occur responsive to a glucose concentration, responsive to a change in state/zone/range of glucose concentration (e.g., between hypo-, hyper-, and euglycemic zones), or responsive to glucose information meeting one or more predetermined criteria (e.g., rate of change of glucose above a threshold). One or more criteria for determining when a transmission from the sensor electronics unit 12 may occur may be user-defined and may be entered on the user interface 512 or entered on a user interface of, e.g., devices 14, 16, 18, or 20. In some embodiments, the wearable device 200 may request transmission of analyte information responsive to an amount of time since a last transmission of analyte information (e.g., more than 20 minutes, 30 minutes, 45 minutes, 60 minutes, etc.), and in this case a clock module 504 associated with the wearable device may be employed to determine such times and durations. Also in some embodiments, the wearable device 200 may request transmission of analyte information responsive to a request by user. A user request may take a variety of forms, such as pressing a button, touching a touch screen, a voice command, or actuating various types of switches. Example switches may be triggered by the wearer's movement, tactile actuation, or the like.

As described above, the alert interface 204 may comprise any of a variety of types of displays, which may form a portion of a user interface 512, and/or may comprise a vibration module 524, a shock module 526, a speaker (not shown), etc. In embodiments including a display, the same may be driven by a display module 514 and configured to provide different types/amounts of information and/or one or more alerts. Such alerts are described in greater detail below, but here it is noted the same may be implemented by, e.g., liquid crystal and light emitting displays 516, e.g., LEDs, LCDs, OLEDs, electronic paper 518, as well as value sensitive material 522, where such material changes color or pattern based on the value of the analyte. Such a user interface may also include a light module driving light pipes 528, discussed in greater detail below with respect to FIG. 3.

In more detail, although a variety of examples are provided herein, the information may be presented in representations that may be sensed by the patient, whether based on values or ranges, or threshold information, or other criteria that may be set by the manufacturer or user. For example, the display's functionality may be limited to simply changing color in response to the signal received from the sensor electronics unit 12, such as displaying a first color, such as green, when the signal indicates that the user's blood glucose is within an acceptable range, and displaying a second color, such as red, when the signal indicates that the user's blood glucose is outside the acceptable range. The color changing functionality may also be further refined to include more colors, such as displaying a first color, such as green, when the signal indicates that the user's blood glucose is within a first narrower range, displaying a second color, such as yellow, when the signal indicates that the user's blood glucose is outside the first narrower range, but still within a second wider range, and displaying a third color, such as red, when the signal indicates that the user's blood glucose is outside the second wider range.

In a further embodiment, an output of the alert interface 204 may be more discreet and pre-programmed by the user.

For example, when one of the low or high thresholds is breached, a first user-programmed pattern may be displayed, and when the other of the low or high thresholds is breached, a second pattern is revealed. The patterns may be customized by the user so that the meaning of each pattern is only known to the user. This embodiment enhances the discreetness of the wearable device 200 because no one else, other than the user, knows the state of the user's glucose.

In the foregoing embodiments, the simplicity and limited functionality of the alert interface 204 reduce the cost and complexity of the wearable device 200, while still providing certain types of users, such as those with type 2 diabetes, with adequate information to manage their condition. In alternative embodiments, the limited functionality of the alert interface 204 may be embodied in something other than a changing color, such as displaying nothing more than a trend arrow (e.g. an arrow indicating whether the user's current blood glucose value is rising or falling, where the arrow points upward to indicate a rising value and downward to indicate a falling value), nothing more than text such as "high," "normal," and/or "low" to indicate the user's current blood glucose value, nothing more than text such as a number corresponding to the user's current blood glucose value, where the number may be color coded (e.g. green for normal, red for high or low) or not, or providing one or more lights that remain solid or blink in response to various conditions. For example, three lights, such as LEDs may be provided, of the same color or different colors. A single blinking light may indicate a hypoglycemic condition, a single solid light may indicate a low glucose condition, two solid lights may indicate that glucose is in the target range, three solid lights may indicate a high glucose condition, and three blinking lights may indicate a hyperglycemic condition. In another example, a progression of lights illuminating may indicate a level of clinical risk, severity of hypo- or hyper-glycemia, rate of change of glucose, etc. For example, lights flashing from left to right or bottom to top may indicate rising glucose, and lights flashing from right to left or top to bottom may indicate falling glucose. Other examples include lights that change size, brightness, and or contrast.

In some embodiments, the alert interface 204 may comprise a light bar, where a percentage of the bar that is illuminated and/or the color of the light may represent the user's glucose level and/or a degree of risk associated with the indicated level. For example, the percentage of the bar that is illuminated may indicate the user's glucose level, while the color of the light bar may indicate the degree of risk associated with the indicated level. A color coded legend may be provided adjacent the light bar to help the viewer interpret the risk level associated with each color. In another example, a colored dot may be shown with a line extending from it, where the color represents risk and the line represents glucose level or range.

Lights may be used in various combinations with vibrations, electrical shocks, and/or audio to indicate any of the above conditions. For example, a blink pattern can be used with one LED. The blink pattern can be used to signify different information. Color1 (such as blue) LED with one blink may be trending low, while Color1 with two blinks may be hypoglycemic. Color2 (such as yellow) LED with one blink may be trending high, while Color2 with two blinks may be hyperglycemic. Other colors may be used to show different system alarms and/or calibration alerts. In another example, a single component LED may display up to three colors. Thus, with one LED and one light pipe, three different colors can be displayed with multiple patterns for each.

In another example, displayed patterns can follow patterns of a "mood ring," e.g. rather than discrete zones (high, target, low), as the user is approaching a different zone, the colors gradually shift. For example, red may indicate high, with shifts to dark pink then mid-pink then light pink as the user enters the target zone. The color may then gradually shift from light pink to white as the user enters the low zone.

In some embodiments, the output to the alert interface 204 may provide positive feedback when the user is performing well, such as when the user stays within a desired glucose range for a set period of time. For example, the alert interface 204 may show a calming or pleasing image such as a tree, a flower, etc., and as the user continues to perform well the image may continue to grow, or may transition from sickly looking to healthy looking. By contrast, if the user is not performing well, the display may provide negative feedback, such as causing the image to shrink, or look sickly, etc. These type of outputs provide cumulative information and/or progress toward a goal, and may be accompanied by additional information, such as a numerical indication of how many days have passed without a high glucose event and/or a low glucose event, a numerical indication of how many high glucose events or low glucose events have occurred within the past few days, weeks, etc., an amount of time spent within a desired range, etc.

The alert interface 204 may include a sleep feature, in which the alert interface 204 automatically dims or darkens after a set interval, and only "wakes up" in response to a user input and/or an alert condition. For example, the wearable device 200 and/or alert interface 204 may include a touch sensor or a button (not shown). Touching the sensor or depressing the button wakes up the alert interface 204 so that the user can view his or her current glucose condition. Such embodiments enhance the discreetness of the wearable device 200 and may also help to conserve battery power.

As discussed above, the alert interface 204 may comprise a speaker for emitting one or more audible alerts. Such alerts may take the form of beeps, or of spoken words, such as "Your glucose is below the acceptable threshold. Please take action." Such alerts may be used in isolation and/or to supplement any visual information provided by the alert interface 204, such as a loud beep when a high or low glucose condition occurs. The volume of the alerts may increase over time until the user takes action. Increasing volume is advantageous, because as glucose levels decrease, cognitive function also decreases. Thus, louder alarms may be more effective at lower glucose levels without increasing any annoyance to the user when glucose is at higher levels. In some embodiments, different visual patterns and/or audible tones may be used to signify different conditions. For example, a first pattern and/or a first tone may be provided for trending low, while a second pattern and/or a second tone may be provided for hypoglycemia, while a third pattern and/or a third tone may be provided for trending high, while a fourth pattern and/or a fourth tone may be provided for hyperglycemia, etc.

The wearable device 200 of FIG. 2 may further comprise a data storage module (not shown), such as flash memory or any other type of data storage. In such embodiments, the sensor electronics unit 124 may send data from the sensor 122 to the communication module 206 so that the data can be stored in the wearable device 200 storage. In such embodiments, the data need not be stored by the sensor electronics unit 124, so that the sensor electronics unit 124 may be simplified and made smaller and less expensive.

Figure 3:
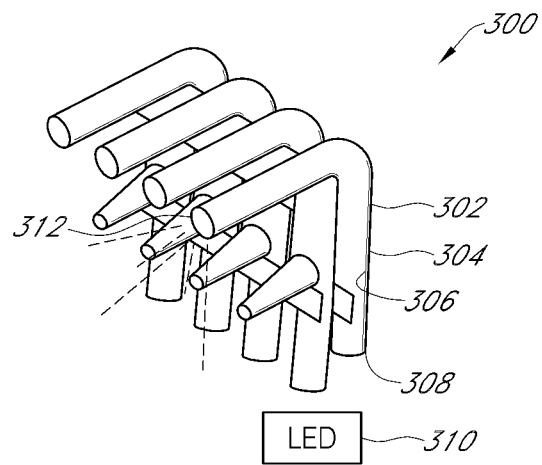
FIG. 3 is a front perspective view of one embodiment of a display for use with the device of FIG. 2.

FIG. 3 illustrates one example of a simple display 300 having limited functionality, and which may comprise the alert interface 204 in the embodiment of FIG. 2. This embodiment comprises one or more light pipes 302, with each light pipe 302 including a tubular portion 304 defining a lumen 306. A first end 308 of the tubular portion 304 receives light from a light source, such as an LED 310, within the wearable device 200. The LED 310 may, for example, be mounted on a printed circuit board (PCB) housed within the wearable device 200. Light from the LED 310 travels through the lumen 306 where it is visible at a second end 312 of the tubular portion 304 that is exposed to the exterior of the wearable device 200. In the illustrated embodiment, a plurality of light pipes 302 are provided, and each light pipe 302 may comprise a different color and/or at least one light pipe 302 may be multicolored. In this embodiment, various combinations of color and/or blink patterns may be used to signify different blood glucose conditions, such as normal, low, high, trending low/high, etc.

As discussed above, in some embodiments the alert interface 204 may comprise a vibration module. In such embodiments, when the communication module 206 receives a signal from the sensor electronics unit 124 that the user's blood glucose is outside of a desired range, or is trending high or low, the controller 208 causes the vibration module to vibrate. The user thus receives a tactile notification, in the form of a vibration on the skin, that his or her blood glucose level may require immediate attention. The user can then take appropriate action, such as taking a finger stick glucose reading. In alternative embodiments, the vibration module may be replaced with, or supplemented with, a shock module for producing an electric shock to the user.

The vibration/shock embodiment(s) is/are particularly useful for times when the user is sleeping, because the wearable device is worn on the body and/or clothing during sleep, and the vibration and/or electric shock is preferably strong enough to wake the sleeping user, and may increase in intensity over time until the user takes action. This embodiment is also particularly useful in social situations where discretion is desired, and in environments where loud noises are not appropriate, such as in a movie theater. In some embodiments, the alert interface 204 may comprise the vibration module and/or the shock module combined with a visual display to provide alerts to the user that are both visual and tactile.

There is an inherent tension between the desire to make CGM receivers smaller and more discreet, and the desire to make CGM receivers capable of providing more information. Some of the present embodiments address this tension by providing a first component that is relatively small and that is worn on, or integrated into, a user's vision [word?], clothes, and/or bodies in such a way so as to physically contact the user's skin during wear, and a second component that is larger than the first component, wherein the first and second components can communicate with one another.

Figure 4:
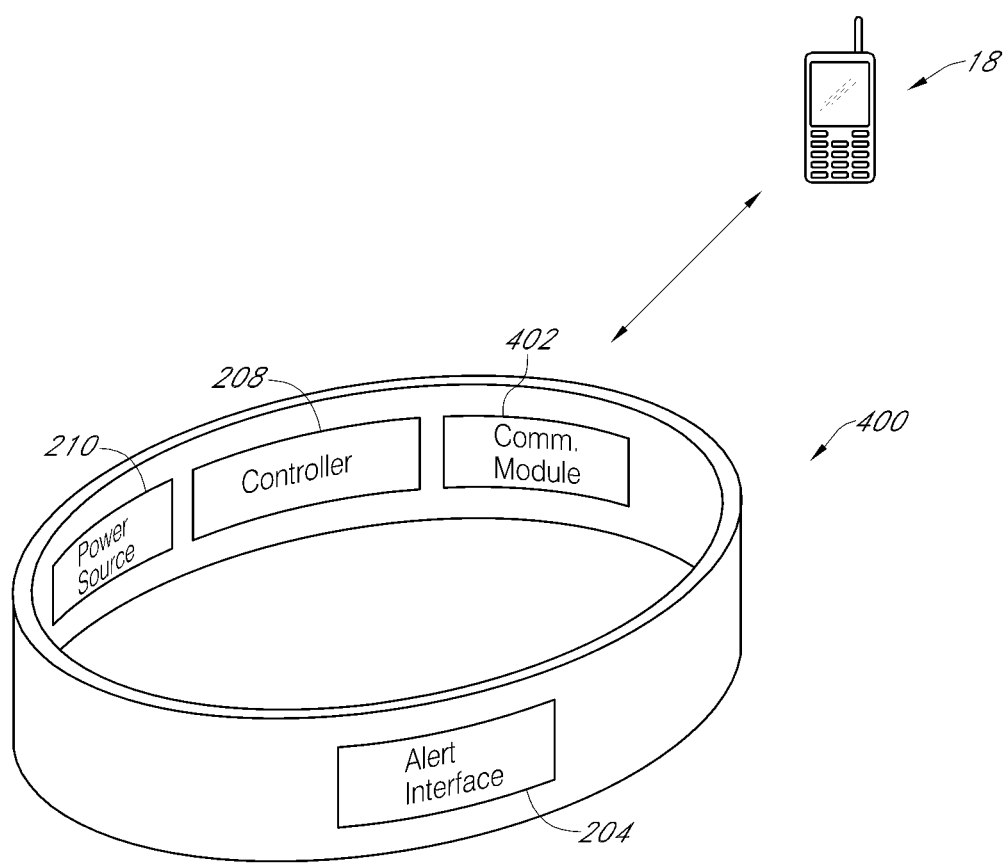
FIG. 4 is a front perspective view of another embodiment of a wearable device for providing a user with an alert.

FIG. 4 illustrates a device 400 for providing a user with an alert. The device 400 includes features that are similar to those of FIG. 2, and their descriptions will thus not be repeated here. In the device 400 of FIG. 4, the communication module 402 has both receive and transmit capabilities. Thus, this embodiment shares the same functionality as the device 200 of FIG. 2, but may also transmit information to one or more other devices. In FIG. 4, only one other device (the smart phone 18 of FIG. 1) is illustrated, but the present embodiments are not limited to this example. The communication module 402 may send signals to any type of other device, including any of those shown and described with respect to FIG. 1. The wearable device 400 of FIG. 4 thus acts as a repeater that receives information from the sensor electronics unit 124 and forwards that information to another device or devices (see in particular device 532 of FIG. 5). In some embodiments, the repeater may store the data received from the sensor electronics unit 124 and relay the data to another device at regular intervals, or whenever the user requests. The repeater may forward the information in the same form in which it was received, and/or may process or partially process the received information before forwarding the processed or partially processed information. Either or both of the wearable device 400 and the other device may then provide an alert, if appropriate. The alert may take any form, such as vibrations, audible tones, and/or visual indicators.

In some embodiments, analyte information may be transmitted from the wearable device 200 and/or received by another device (e.g. a display device, a cloud-based device, etc.) at regular intervals, such as every 30 seconds, every 60 seconds, every 90 seconds, every 2 minutes, every 3 minutes, every 5 minutes, every 10 minutes, every 15 minutes, every 20 minutes, every 30 minutes, or at any other regular interval. Also in some embodiments, analyte information may be transmitted from the wearable device 200 and/or received by another device in response to a trigger. A variety of triggers are contemplated. For example, analyte information may be transmitted and/or received whenever the user requests. In other examples, a transmission from the wearable device 200 may occur responsive to a glucose concentration, responsive to a change in state/zone/range of glucose concentration (e.g., between hypo-, hyper-, and euglycemic zones), or responsive to glucose information meeting one or more predetermined criteria (e.g., rate of change of glucose above a threshold). One or more criteria for determining when a transmission from the wearable device 200 may occur may be user-defined. In some embodiments, another device, such as a device in the cloud, may request transmission of analyte information responsive to or based on an amount of time since a last transmission of analyte information (e.g., more than 20 minutes, 30 minutes, 45 minutes, 60 minutes, 1 day, etc.) Also in some embodiments, a smartphone and/or network may request transmission of analyte information, such as when a smartphone application is initiated and/or when a network makes a request.

The ability of the wearable device to repeat data from the sensor electronics unit 124 to another device also solves the problem of communication between different wireless protocols, such as between a manufacturer-specific medical device and a generic handheld consumer device (e.g., a mobile phone). Because handheld consumer devices use many different wireless technologies, the ability of the manufacturer-specific medical device to communicate with every available consumer device on the market is limited. As such, the wearable device may provide not only an alert interface, but also connectivity from the manufacturer-specific medical device to any of a wide variety of consumer devices. As one example, a manufacturer may provide a proprietary RF protocol from the sensor electronics unit to the wearable device, and the wearable device may be embedded with BLUETOOTH® technology for connectivity to certain mobile phones, enabling the sensor electronics unit to communicate with a consumer device that uses a wireless technology that is incompatible with the sensor electronics. The sensor electronics unit and the wearable device may be embedded with any combination of one or more, or two or more, of the following different communication protocols, respectively, including: Radio frequency, infrared (IR), magnetic induction, BLUETOOTH®, BLUETOOTH® low energy (BLE), near field communications (NFC), body area network (BAN), universal serial bus (USB), any of the wireless local area network (WLAN) communication standards, including the IEEE 802.11, 802.15, 802.16, 802.20, 802.22, and other 802 communication protocols, ZIGBEE®, wireless (e.g., cellular) telecommunication, paging network communication, magnetic induction, satellite data communication, general packet radio service (GPRS), the ANT protocol, and/or a proprietary communication protocol.

In embodiments in which data is forwarded from the wearable device 200 to another device upon user request, the request may be initiated using the wearable device 200 and/or the other device. For example, the wearable device 200 may include a button (not shown) or other input mechanism that the user manipulates to initiate the data transfer from the wearable device 200 to the other device. Instead, or in addition, the other device may include a button (not shown) or other input mechanism that the user manipulates to initiate the data transfer from the wearable device 200 to the other device. The wearable device 200 may also include one or more buttons (not shown) for activating/silencing alarms/alerts and/or powering on/off the wearable device and/or connecting to the transmitter or receiver.

In any of the foregoing embodiments, the type of alert provided by the wearable device may be configurable. For example, the user may select one or more different types of alerts, such as audible alerts, visual alerts, and/or tactile alerts. Selections may be made using only the wearable device, and/or the wearable device may be connectable to a computing device and selections may be made using the computing device and then the selections stored on the wearable device through a wired or wireless connection. Various other settings may also be programmable, such as varying the intensity of alerts based on a time of day, or increasing the intensity of alerts when the user does not respond to a given alert within a set interval, where the duration of the interval may also be set by the user.

In any of the present embodiments, any component of the sensor system may change color to reflect the user's current glucose level. For example, one color may be shown if the level is low, another color if the level is in a predefined range, and another color if the level is high. As the level increases or decreases, the intensity and/or brightness of the colors could also increase or decrease. The color could also blink or have different pulse patterns for other indications, such as a low glucose limit.

Figure 6:
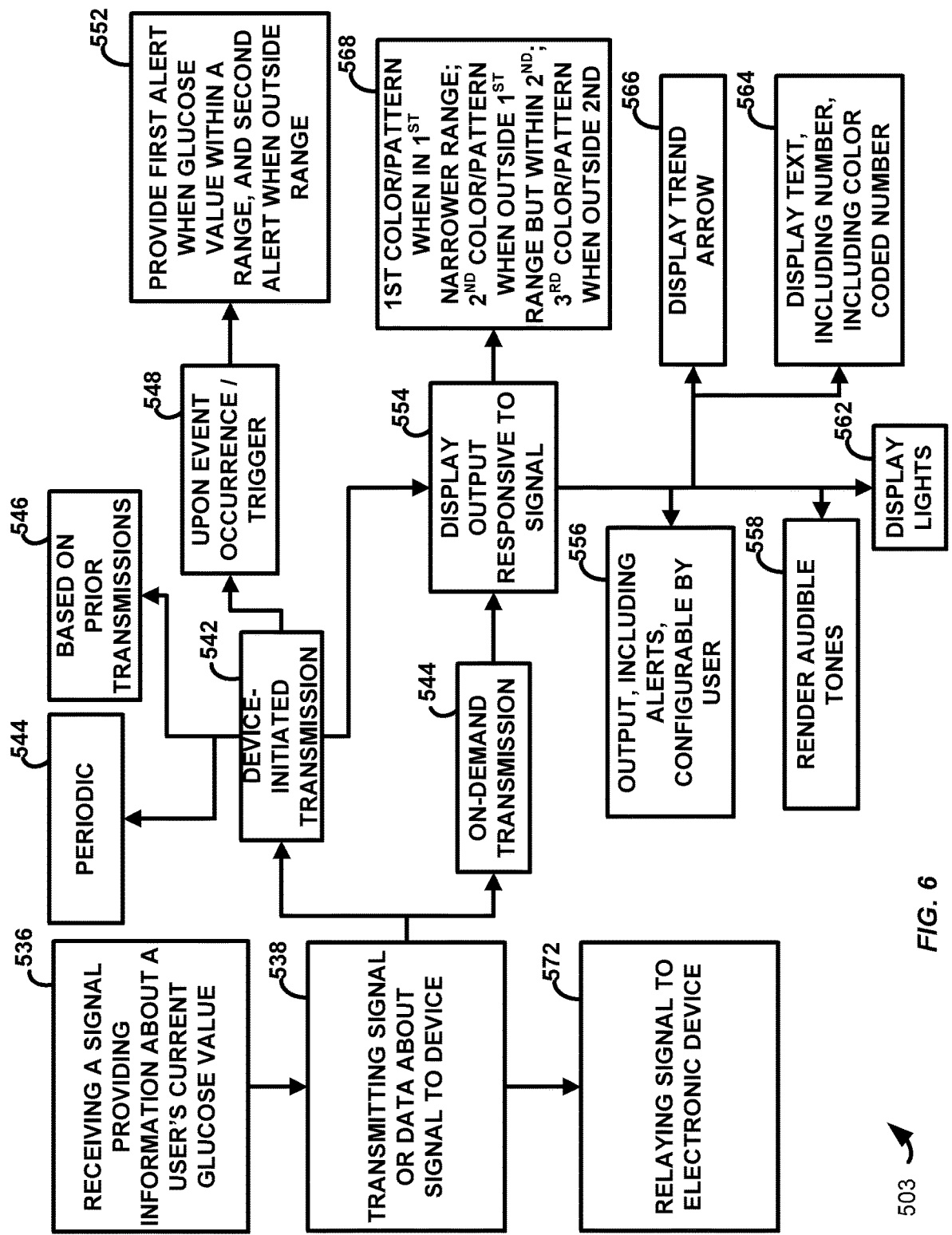
FIG. 6 is a flowchart illustrating a method of use according to an embodiment of a wearable device for providing a user with an alert.

FIG. 6 is a flowchart 503 illustrating a method according to present principles. In a first step, a signal is received providing information about a user's current analyte value, e.g., glucose (step 536). The same may then be transmitted to the device, e.g., a wearable device 200, for display in some fashion (see above) to the user (step 538). Of course, it will be understood that sensor electronics and/or the receiving device, e.g., the wearable device 200, may perform some level of processing on the signal prior to its indication to the user on a display. The processing and display of the measured analyte signal on the wearable device provides for a smaller form factor and yet still provides the user with useful and actionable information. As the sensor assembly is coupled to the patient (and indeed the sensor is within the patient), and yet the display is, e.g., coupled to the limb of a user, wireless transmissions are generally required and the computing environments described may provide for such. The transmissions further allow the determination and display of useful information on a device coupled to a limb of the user, e.g., their wrist.

Transmissions to the device may either be device-initiated (step 542) or on-demand (step 544). In the former, it is noted that the "device" is generally the sensor electronics. Device-initiated transmissions may be periodic (step 544), e.g., transmitted every hour, every half-hour, every 30 minutes, every 15 minutes, every 10 minutes, every 5 minutes, and so on. Alternatively device-initiated transmissions may happen upon the occurrence of an event, i.e., a trigger (step 548). For example, a first alert may be provided when the measured glucose concentration value is within a predetermined range, and a second alert may be provided when the glucose concentration value is outside of the predetermined range (step 552). Device-initiated transmissions may also occur based on the occurrence of prior transmissions (step 546). For example, a long period of time has elapsed since the last device-initiated transmission, such may be used as a basis to determine when the next device-initiated transmission should occur.

Whether transmission is on-demand (step 544) or device-initiated (step 542), an output may be displayed responsive to the glucose concentration signal (step 554). Such outputs may include audible tones (step 558), displayed lights (step 562), or trend arrows (step 566). The display may also include a display of text (step 564). The text may provide a verbal indicator of a user status, but may also include numbers, and in other implementations such numbers may be color-coded in manners noted above (step 564).

In a specific implementation (step 552), a first color or pattern may be displayed when the analyte value is within a first relatively narrow range. A second color or pattern may be provided when the analyte value is outside of the first relatively narrow range, but within a second range, wider than the first. A third color or pattern may be provided when the analyte value is outside of the second range. Numerous variations of the above will also be understood.

Yet another step, which is optional, and which may be performed by the wearable device or by the sensor electronics, or both, may include relaying the signal, or data about the signal, to another electronic device (step 572). Such other devices may include smart phones, personal computers, tablet computers, and the like. In this way, analyte data may be conveniently viewed by a user but also forwarded to another device for, e.g., permanent storage, analysis including retrospective analysis, and so on.

Finally, it is noted that the systems and devices of FIGS. 1-5 may generally perform one or more of the steps shown in FIG. 6, and that the steps shown may be performed by the systems and devices of FIGS. 1-5, as well as other properly configured systems and devices. In some cases, systems and devices, e.g., programmable watches, programmable eyewear, hats, and the like, may be configured with appropriate sensors and/or programming to perform the steps noted. In some cases, a non-transitory computer readable medium may be configured with instructions which cause a computing environment to perform one or more of the steps shown in FIG. 6.

Also in any of the present embodiments, the wearable device may include additional functional components, such as a pedometer, a mechanism that detects movement, acceleration, orientation, etc., such as an accelerometer and/or a gyroscope, a start/stop exercise button, etc. The advantages of the foregoing components are explained in greater detail in U.S. patent application Ser. Nos. 13/801,445, 13/802,424, 13/802,237, and 13/802,317, all filed on Mar. 3, 2013, the entire disclosures of which are hereby incorporated by reference herein and made a part of this disclosure.

In addition to the advantages described in the foregoing applications, the following advantages may also be realized in the present embodiments. A component such as an accelerometer may detect the user's activity level and adjust an output and/or an alert accordingly. For example, if the accelerometer detects that the user is active (moving), a visual alert may be output to the alert interface 204. By contrast, if the accelerometer detects that the user is not active (may be sleeping), an alert may be output to the alert interface 204 in the form of an audible tone, a vibration, and/or an electric shock, because a sleeping user is unlikely to notice a visual alert, but a loud beep, a tactile sensation, and/or an electric shock are much more likely to grab the user's attention.

In the present embodiments, the system may be capable of communicating with a network 534 comprising other users of CGM devices (see again the system 501 of FIG. 5, and in particular devices 534). For example, the system may be able to detect the user's location, and the locations of other users in the network. Location information can then be used to provide the user with further information, such as locations of other users who may be able to help the user in the event of an emergency, such as a hypoglycemic event. The network may further be able to use the location information to send alerts to the user and/or to other users that someone in their vicinity is in need of help.

In embodiments that communicate with a network, the user may be able to see data/information about other users in the network that can enhance the user's experience. For example, the user may set goals and/or compete with friends or as teams. Further, the network may provide a remote monitoring system for family/friends/loved ones, or even a professional/clinical remote monitoring service, including potentially connected multiple-disease states (e.g., diabetes and cardiac monitoring).

In one example a user may program his or her device to communicate with selected followers, and if the user does not acknowledge an alarm, the followers are notified. The followers may be grouped in various ways, such as by proximity so only those that are nearby are notified. Alternatively, the followers may be grouped by common activity, such as the user's coworkers, athletic group, teammates, etc. Followers could also be notified via an online calendar in which the system knows certain followers are in a work meeting based on entries in the calendar so that only those coworkers that were also invited to that meeting are notified. In another example, the system knows that the user is scheduled to meet friends, and only those friends are notified, again based on entries in the calendar. Further, if the system knows the user is severely low, it can notify paramedics and/or activate various other systems, such as unlocking the user's front door, turning on the user's front door light, etc. In one example, the system may communicate with other systems via the Internet. In a further example, the system may unlock the user's front door and turn his or her front door light green so that when the paramedics are notified, they are also notified to come to the house on Smith Street with the green porch light. Separately, the system can be inclusive of strangers also on the system so that they are notified only when someone nearby needs help. The helper may then receive points on their profile as a reward for helping another user.

In various other embodiments, the communication module 206 may be used in conjunction with a contacts module (not shown) to provide updates to a social network. In some embodiments, the user's location and/or other attributes associated with the user (such as type of diabetes, age, sex, demographic, etc.) and/or the CGM device can be used to find other people in the area with similar attributes and/or using a similar CGM device, to recommend as a social connection. For example, the communication module 206 in connection with a social media network may enable the user to select from options such as finding other people with diabetes, or finding other people with diabetes near the user, or finding recommendation of diabetes-friendly restaurants in the area, etc.

In some embodiments, the communication module 206 enables a user to selectively upload or share information from device electronically and/or via a social network. Example information that could be shared includes a success metric, a current EGV value, a screen shot, an achievement, an award, a pattern trend graph, activity information, location information, and/or any other parameter described as a possible input into or output from the communication module 206 elsewhere herein. For example, the communication module 206 may have user selectable actions such as share EGV on Facebook, share EGV on Twitter, share screen via Facebook, Twitter, e-mail, MMS, send trend screen to printer, etc. Additionally, or alternatively, the communication module 206 may enable a user to add preset and/or custom captions, or change a status with their shared information, such as "check out my no hitter," which can be shared selectively (by a user or based on parameters) and/or automatically. In one example, a user can "like" a particular CGM from the communication module 206 directly to a particular social site. In certain embodiments, when the user selects to share information, options may be shown on the alert interface 204 that enable the user to select what to share and with whom. The user may predefine groups and or individuals to share information with. For example, the user may create a group of friends, and when the user chooses to share something he or she selects to share it with the predefined friends, and a notification is then sent to each person in the group. This functionality is useful, for example, for parents who want to monitor their child's blood glucose. The child can choose to share a BG value, and then select parents, or mom, or dad, and the BG value is then sent to the selected person(s).

In some embodiments, the communication module 206, in concert with a social network, can be configured to allow users to compare EGV, trends, number of lows, etc. with friends or a group on the social network site (e.g., Facebook, Twitter, etc.). In some embodiments, the system 100, using CGM information from a plurality of users, compares one or more parameters to determine a comparison of data from a single person to the average (grouped by some similarity, for example). In some embodiments, the system 100 calculates achievements, points, badges, or other rewards based on predetermined criteria (keeping blood glucose in a target range, use of CGM, etc.), which can be selectively or automatically posted to a social network site (e.g., Facebook, Twitter, etc.). In some embodiments, when a user would like to share a learning from the system 100, e.g., a picture of food and resulting EGV or trend graph, the system 100 enables the user to selectively upload the information to a site. In this context a learning is an event or a first situation, and the effect, output, or trend resulting therefrom.

Additionally or alternatively, data from CGM users can be aggregated, whereby the system 100 is configured to enable a user to query for current active CGM users, xx % of people using a CGM that are in range, other CGM users with a similar glucose as him or her (within a margin of error, such as 80 mg/dL±5), etc. These queries can also be narrowed by geography, by doctor, age, gender, ethnicity, diabetes type, therapy type (pump, syringes, exenatide, metformin, etc.), etc.

In some embodiments, a communication module on a first smartphone communicates with another communication module on a second smartphone (e.g., via a social network site or other network connection) to allow CGM users to play or compete with others in a group (or with a particular friend) with one or more metrics (e.g., amount of time in target range, reduction of hypoglycemia, continuous use of CGM, etc.).

In some embodiments, the system 100 allows users to share problems or difficulties associated with their device(s) and/or disease management by uploading screen shots, questions, data, etc. Further, the system 100 may allow others to post solutions or answers to similar problems, which solutions or answers may be sent to a smartphone for local review by the sharer.

In some embodiments, the system 100 comprises a database of doctors that treat patients using CGM (prescribe CGM), and which allows a user to find a CGM-prescribing doctor within a defined distance. In various embodiments, the system 100 enables a user to "pin" (using a site such as Pinterest) a CGM screen shot, trend graph, etc. that results from cooking and consuming a recipe, for example, a recipe for eggs that also includes the CGM graph of what the recipe did to the user's glucose.

The following are some examples of activities that may be considered quantifiable achievements, and that could be used by the system 100 to reward the user, and/or could be uploaded to share or compete with others: First sensor worn, one-month streak of continuous wear, two-month streak of continuous wear, x-month streak of continuous wear, one-year CGM anniversary, two-year CGM anniversary, x-year CGM anniversary, no-hitter day (e.g., no glucose values below a predetermined hypoglycemic threshold), no-hitter two-day streak, no-hitter x-day streak, quickly curbed a high (e.g., above hyperglycemic upper target for no more than 20 minutes, 40 minutes, 60 minutes, etc.), quickly corrected a low (below hypoglycemic lower target for no more than 20 minutes, 40 minutes, 60 minutes, etc.), fixed a problem area (when the pattern report indicates a pattern, then the pattern no longer appears), the fixed problem area could generate an alert, first upload (if not automatically uploaded), $n^{th}$ upload, shared CGM information with a friend (e.g. screenshot), posted CGM trend on a social media site, no highs today, no highs in x days, no double arrows day (e.g., rate of change of glucose levels stayed below a threshold), longest time in desired range (longest in-range time is x hours), most screen views in a day, longest time without data gaps (e.g. not being out of range). In some cases, such as longest time, challenges could be a stored record that a user would try to beat.

The embodiments described above provide a wearable device that is smaller and has limited functionality as compared to a typical receiver of a CGM system. The wearable device can thus be worn discreetly to preserve the wearer's privacy regarding his or her health condition(s), and to save the user form embarrassment in certain social situations. Certain embodiments may also be water resistant, so that the wearable device can be worn during activities where a typical receiver would normally be set aside, such as water activities (swimming, bathing, etc.). Certain of the present embodiments may be used in place of a typical receiver, or as a supplement to a typical receiver.

The embodiments described above provide a further advantage in that they can be worn on the body, and thus can follow the user wherever he or she goes. As long as the user does not deliberately remove the wearable device, it will remain with him or her at all times, reducing the likelihood that the user will fail to receive an alert when his or her blood glucose is above or below a threshold value and/or trending high or low. Further, as long as the wearable device is being worn, it will always be in close proximity to the sensor electronics unit/transmitter. The transmitter can thus be tailored to be very small and to operate on very little power, because it need only communicate with the wearable device, which is always in close proximity. And with embodiments in which the wearable device is capable of storing data, the transmitter can send the data to the wearable device for storage so that the sensor electronics unit does not need to include any data storage, further enhancing the ability to reduce the size of the sensor electronics unit.

The present embodiments may also be integrated with an IFTTT ("IF This, Then That") protocol to provide the user with additional forms of alerts. For example, a user may program his or cellular phone with an IFTTT protocol that provides a phone call, e-mail, text message, etc. whenever the user does not respond to a given condition within a certain interval after the wearable device provides an alert. After the allotted interval has passed, the communication module then sends a notification to the user's IFTTT network, which then provides an additional alert through another device. For example, one such IFTTT protocol may be to provide the user with a phone call if he or she doesn't respond to a hypoglycemic alert within five minutes. In another example IFTTT protocol, in response to an alert, such as a hypoglycemic condition, the IFTTT protocol may unlock a door to the user's home, and provide an alert to a neighbor of the user that the user needs help. The user can thus be reassured that potentially dangerous conditions will be caught, even when the user is asleep.

The present embodiments may also be capable of communicating with one or more other medical devices that are on or within the user. For example, some diabetics wear an insulin pump. When the wearable device receives a signal from the sensor electronics unit 124 that indicates the user's blood glucose is rising, the wearable device may send a signal to the insulin pump to administer an appropriate quantity of insulin to the user and/or alert the user of changes to the insulin pump administration (e.g., in a semi-closed loop or closed loop configuration).

The present embodiments may also be able to leverage social media to create additional advantages. For example, a user may make his or her data available to select users on a social media network, such as Facebook, Twitter, etc. Data from all users in the group may also be available to all other users in the group. Various types of competitions could then be organized, such as team competitions to determine a winning team based on glucose level performance. Such competitions would not only provide additional motivation for users to diligently monitor their blood glucose, but would also provide a sense of accomplishment when positive results are achieved. Social networking applications may also be used to alert all people within a given proximity, or to alert only nearby people who have indicated a willingness to participate in monitoring a given user.

The present embodiments may include one or more features that reduce the burden on the user. For example, the wearable device may include a microphone and circuitry to enable voice recognition so that the user can issue commands to the system easily by speaking into the microphone.

Such features that make using the system easier increase the likelihood of patient compliance. In another example, the system may display information when it detects movement, such as in the user's hand and/or wrist, which may indicate that the user is looking at the system. Certain gestures may be used to activate and/or inactivate the alert interface, including waking up the display and/or acknowledging an alert. By increasing convenience to the user, additional, e.g., redundant, user data entry is minimized, reducing the load on applicable computing environments and causing the same to operate in a more efficient manner.

The embodiments described above may also provide the following further advantages: Because the device is wearable, the display is easily visible without a need to touch the device with either hand; Only the user may be aware of any alerts provided by the wearable device, so that the user is not embarrassed by alerts in social situations; The option to configure different types of alerts, such as audible, visual, and/or tactile; The wearable device may detect when the user is asleep and make appropriate adjustments to basal thresholds and/or rates based on the detected condition rather than making assumptions based on the time of day; The wearable device may detect when the user is asleep and automatically make adjustments to the alert notifications, such as the volume or intensity thereof, to increase the likelihood that the user will wake up in response to an alert; Where data is forwarded from the wearable device to another device, such as a cellular phone, the user can discreetly review the data in private at any convenient time.

In certain embodiments, the repeater electronics could be snapped into a wearable device or a keychain, for example. This would allow the user to choose how they wanted to use the repeater at different times and/or so that the wearable device could be generic, while the repeater electronics could be exchanged depending on the type of wireless protocol used (e.g., depending on whether the user needs to transmit to a Galaxy phone (ANT+) or an iPhone (BLE)).

Any of the embodiments described herein may be configured to provide information representative of glucose information. For example, the information may be embodied in one or more of a graphical representation, a numerical representation, a representation indicative of glucose concentration, information indicative of a glucose state, a glucose range, or a glucose zone, and/or information indicative of glucose meeting one or more predetermined criteria, wherein the criteria may be user-definable. Glucose states are described in U.S. patent application Ser. No. 13/742,694, filed on Jan. 16, 2013, the entire contents of which are incorporated herein by reference and made a part of this disclosure.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus, and/or device (e.g., magnetic disks, optical disks, memory, programmable logic devices (PLDs)) used to provide machine instructions and/or data to a programmable processor, including a machine-readable medium that receives machine instructions.

While specific examples have been provided herein for illustrative purposes, it is understood that to provide for interaction with a user, the subject matter described herein may be implemented on a computer having a display device (e.g., a CRT (cathode ray tube), LED (light-emitting diode), or LCD (liquid crystal display) monitor) for displaying information to the user and a keyboard and a pointing device (e.g., a mouse or a trackball) by which the user may provide input to the computer. Other kinds of devices may be used to provide for interaction with a user as well, for example, feedback provided to the user may be any form of sensory feedback (e.g., visual feedback, auditory feedback, or tactile feedback), and input from the user may be received in any form, including acoustic, speech, or tactile input.

Further, while specific examples have been provided herein for illustrative purposes, it is understood that the subject matter described herein may be implemented wholly or in part using a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

In some implementations, the continuous analyte sensor system includes a DexCom G4® Platinum glucose sensor and transmitter commercially available from DexCom, Inc., for continuously monitoring a host's glucose levels.

In some embodiments, the system may execute various applications, for example, a CGM application, which may be downloaded to the receiver or other electronic device over the Internet and/or a cellular network, and the like. Data for various applications may be shared between the device and one or more other devices/systems, and stored by cloud or network storage and/or on one or more other devices/systems. The data so stored may form the basis of the dynamic reports described above.

The connections between the elements shown in the figures illustrate exemplary communication paths. Additional communication paths, either direct or via an intermediary, may be included to further facilitate the exchange of information between the elements. The communication paths may be bi-directional communication paths allowing the elements to exchange information.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure (such as the blocks of FIG. 5) may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise various types of RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

The system and method may be fully implemented in any number of computing devices. Typically, instructions are laid out on computer readable media, generally non-transitory, and these instructions are sufficient to allow a processor in the computing device to implement the method of the invention. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file-storing medium. The outputs may be delivered to a user by way of a video graphics card, graphics processor, or integrated graphics chipset coupled to a display that maybe seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or WiFi-connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred,'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Other implementations may be within the scope of the following claims.

The above description presents various embodiments of the present invention, and the manner and process of making and using them, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

What is claimed is:

1. A wearable device for providing an alert to a user regarding a wearer's blood glucose value, the device comprising:
    a communication module comprising circuitry for receiving a signal from a transmitter of a continuous glucose monitoring device, wherein the communication module is configured to relay the signal received from the transmitter to one or more remote monitoring devices monitoring the wearer's blood glucose state corresponding to the wearer's blood glucose value;
    an alert interface configured to provide a first alert when the wearer's blood glucose value is within a predetermined range, and a second alert that the wearer's blood glucose value is outside the predetermined range, wherein the alert interface has limited functionality compared to that of the one or more remote monitoring devices; and
    wherein the communication module circuitry is further configured to detect the location of the wearer and the location of the one or more remote monitoring devices, and determine a set of the one or more monitoring devices proximate to the wearable device, and is further configured to send signals to the set of the one or more remote monitoring devices in response to detecting that the wearer has not acknowledged an alert provided at the alert interface.

2. The wearable device of claim 1, further comprising a band configured to be worn about a wrist of a wearer, wherein the communication module and the alert interface are incorporated into the band.

3. The wearable device of claim 2, wherein the band comprises a closed loop having no endpoints.

4. The wearable device of claim 3, wherein the band is constructed of a resilient material.

5. The wearable device of claim 1, wherein the alert interface comprises a display including at least one of a liquid crystal display, one or more light-emitting diodes, one or more organic light-emitting diodes, an electronic paper display, a color- or pattern-changing material, or a text display.

6. The wearable device of claim 1, wherein the device is configured to process or partially process data received from the transmitter prior to relaying it.

7. The wearable device of claim 1, wherein the communication module is configured to store data received from the transmitter and relay the data upon a user request.

8. The wearable device of claim 7, wherein a user request to relay the data may be initiated using the device.

9. The wearable device of claim 1, wherein the communication module is configured to relay the signal received from the transmitter in response to a trigger.

10. The wearable device of claim 9, wherein the trigger comprises a user request, a glucose concentration, a change in state or zone or range of a glucose concentration, or glucose information meeting one or more predetermined criteria.

11. The wearable device of claim 1, wherein a functionality of the alert interface is limited to providing positive feedback when the wearer's blood glucose remains within a desired glucose range for a set period of time, and providing negative feedback when the wearer's blood glucose is outside the desired glucose range.

12. The wearable device of claim 1, wherein the device is configured to be in physical contact with skin of a wearer at all times when worn by the wearer.

13. A method of providing an alert to a user regarding a wearer's blood glucose value, the method comprising:
    receiving a signal providing information about the wearer's current blood glucose value, and relaying the received signal to one or more remote monitoring devices monitoring the wearer's blood glucose state corresponding to the wearer's blood glucose value;
    on an alert interface having limited functionality compared to that of the one or more remote monitoring devices, providing a first alert when the wearer's current glucose concentration is within a predetermined range, and a second alert when the wearer's current glucose concentration is outside the predetermined range;
    detecting a location of the wearer and a location of the one or more remote monitoring devices;
    determining a set of the one or more monitoring devices proximate to the wearable device; and
    sending signals to the set of the one or more remote monitoring devices in response to detecting that the wearer has not acknowledged an alert provided at the alert interface.

14. The method of claim 13, further comprising processing or partially processing data received from the signal prior to relaying it.

15. The method of claim 13, further comprising storing data received from the signal and relaying the data when the user requests.

16. The method of claim 13, the signal is received using a first wireless communication protocol and relayed using a second, different, wireless communication protocol.

17. The wearable device of claim 1, wherein at least one of the one or more remote monitoring devices is a device associated with the wearer and at least another one of the one or more remote monitoring devices is a device associated with a user different than the wearer.

* * * * *

UNITED STATES PATENT AND TRADEMARK OFFICE
CERTIFICATE OF CORRECTION

PATENT NO. : 10,729,388 B2
APPLICATION NO. : 14/524919
DATED : August 4, 2020
INVENTOR(S) : Eli Reihman et al.

It is certified that error appears in the above-identified patent and that said Letters Patent is hereby corrected as shown below:

In the Drawings

In sheet 5 of 5, FIG. 6, reference numeral 568, Line 1, delete "1ST" and insert --$1^{ST}$--.

In the Specification

In Column 3, Line 39, delete "value" and insert --value.--.

In Column 8, Line 11, delete "Co A;" and insert --CoA;--.

In Column 8, Line 27, delete "andrenostenedione;" and insert --androstenedione;--.

In Column 8, Line 42, delete "diptheria" and insert --diphtheria--.

In Column 8, Lines 47-48, delete "uridyltransferase;" and insert --uridylyltransferase;--.

In Column 8, Line 49, delete "perioxidase;" and insert --peroxidase;--.

In Column 8, Line 58, delete "sissomicin;" and insert --sisomicin;--.

In Column 8, Lines 62-63, delete "duodenalisa," and insert --duodenalis,--.

In Column 9, Line 3, delete "Trepenoma pallidium," and insert --Treponema pallidum,--.

In Column 9, Line 4, delete "stomatis" and insert --stomatitis--.

In Column 9, Line 25, delete "(barbituates," and insert --(barbiturates,--.

In Column 9, Line 41, delete "(FHIAA)." and insert --(5-HIAA).--.

Signed and Sealed this
Sixth Day of October, 2020

Andrei Iancu
*Director of the United States Patent and Trademark Office*

CERTIFICATE OF CORRECTION (continued)
U.S. Pat. No. 10,729,388 B2

In Column 15, Line 42 (approx.), delete "and or" and insert --and/or--.

In Column 22, Line 35, delete "and or" and insert --and/or--.

In Column 29, Line 39, delete "preferred," and insert --'preferred,'--.